US00PP07995P

United States Patent [19]

Strahle

[11] Patent Number: Plant 7,995

[45] Date of Patent: Oct. 6, 1992

[54] HYBRID TEA ROSE PLANE CARBANE

[75] Inventor: Glen Strahle, Carlton, Oreg.

[73] Assignee: Carlton Rose Nurseries, Inc., Carlton, Oreg.

[21] Appl. No.: 619,563

[22] Filed: Nov. 29, 1990

[51] Int. Cl.[5] ..... A01H 5/00
[52] U.S. Cl. ..... Plt./19
[58] Field of Search ..... Plt./19, 20

[56] References Cited

U.S. PATENT DOCUMENTS

P.P. 3,078 10/1971 Kondes ..... Plt. 19
P.P. 4,241 4/1978 Van Veen ..... Plt. 18

OTHER PUBLICATIONS

Haring, P. A. (Editor), "*Duchess*" *Modern Roses* 9, The American Rose Society, Shreveport, La., 1986, p. 81.
Anon. 'Duchess' *Modern Roses* 8, The McFarland Co., Harrisburg, Pa., 1980, p. 120.

*Primary Examiner*—James R. Feyrer
*Attorney, Agent, or Firm*—Chernoff, Vilhauer, McClung & Stenzel

[57] ABSTRACT

A vigorous rose plant of the hybrid tea class, a sport from a rose plant entitled "Duchess" provides abundant long-lasting vibrant reddish-pink flowers which substantially maintain their true color from flower opening through petal drop on a continuous basis when grown in a greenhouse.

2 Drawing Sheets

BACKGROUND AND SUMMARY OF THE INVENTION

The present invention relates to a new and distinct variety of hybrid tea rose plant. The object of the present invention is to provide a rose plant of the hybrid tea class which is capable of freely yielding quality-cut flowers under greenhouse conditions.

The primary features of this new variety which connotates its distinctive advance over previously existing types is its ability to produce an abundance of flowers having a vibrant reddish-pink color which remain true after being cut from when they first open through petal drop from a plant which will continuously yield cut flowers under greenhouse conditions.

The variety of rose plant of the present invention was found in a commercial greenhouse at Carlton, Ore. in 1987 as a very distinctive color sport from a plant entitled "Duchess," U.S. Plant Pat. No. 4,241.

*Modern Roses* 9 at page 81 lists "Duchess" as a hybrid tea, color class medium pink. Carbane is a spontaneous mutation and differs from the mother plant only in the color of blooms produced, Carbane having a much darker, almost red, bloom.

Asexual reproduction of this new variety in Wasco, Calif., by means of budding, shows that its unique characteristics come true to form and is establishes and transmitted through succeeding propagations through budding.

BRIEF DESCRIPTION OF THE DRAWINGS

In the accompanying drawings typical specimens of the vegetative growth and flowers of the new variety are shown in different stages of development and are depicted in color as nearly true as is reasonably possible to make in color illustrations of this character.

DETAILED DESCRIPTION OF THE DISCLOSURE

Figure 1:
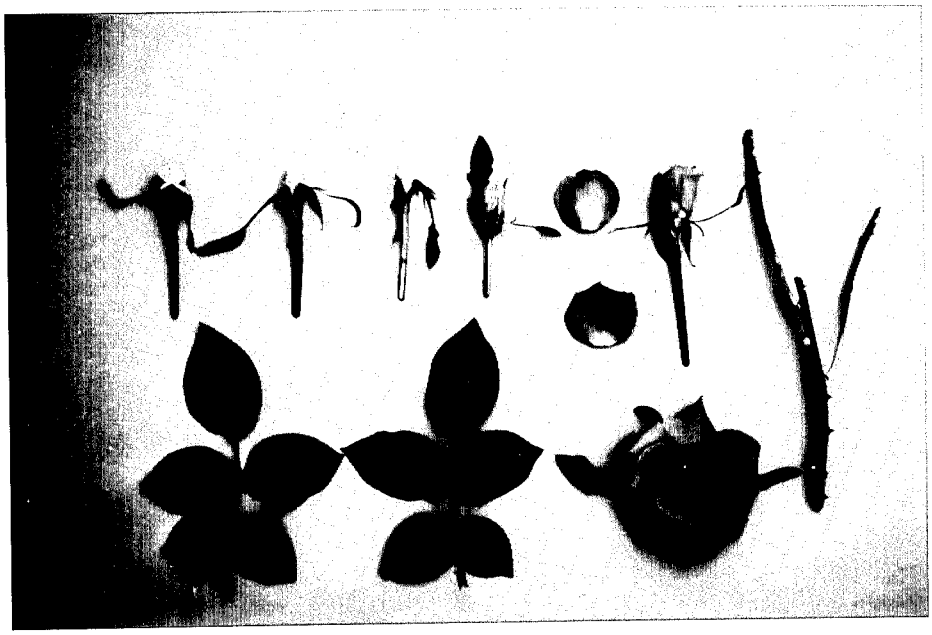
FIG. 1 depicts parts detached from the plant including, progressively, in the top row, flower stems (in side view) having, from left to right, petals removed, a flower stem and receptacle having petals and stamens removed, a receptacle split in cross section, two petals showing bottom (top) and top (bottom) surfaces, a flower stem and flower stem and flower in half-open stage. The bottom row depicts the bottom view of a five-leaflet leaf, the top view of a five-leaflet leaf, a face view of a fully opened flower, and a portion of a detached stem with foliage removed to depict thorns and stem coloration.
Figure 2:
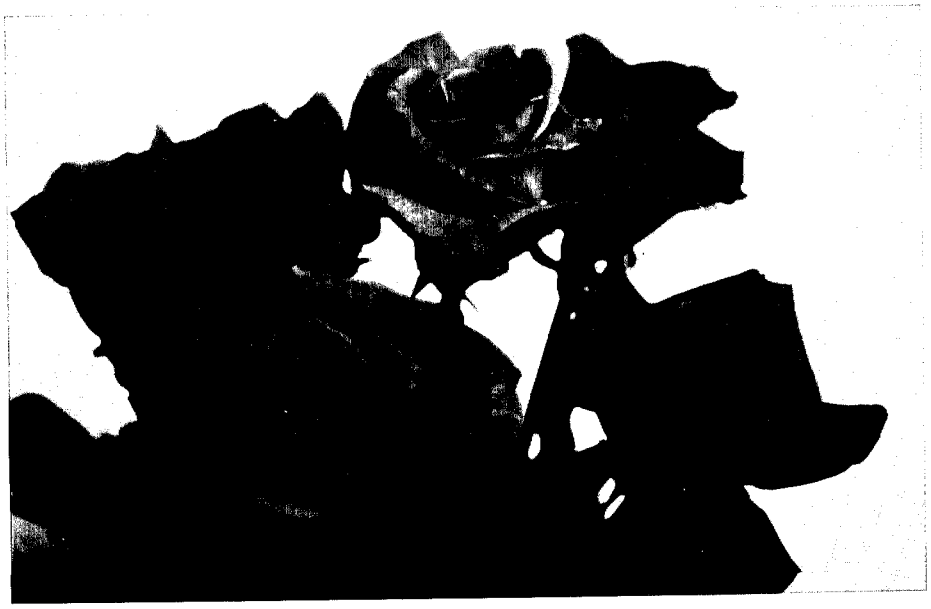
FIG. 2 shows a bouquet of flowers of Carbane in various stages of opening.
Figure 3:
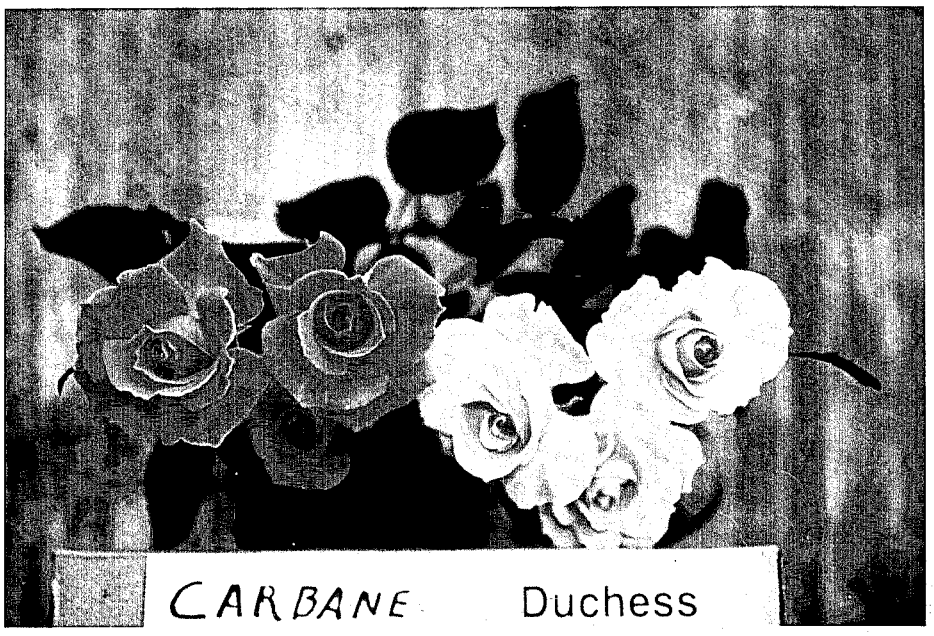
FIG. 3 shows the plant on the left and the "Duchess" parent on the right.

The following description was made during November 1989 of rose plants of the new and distinct variety growing in a greenhouse at Carlton, Ore. Color designations are to The Royal Horticultural Society Colour Chart.

FLOWER

Flowers borne: Singly on strong, long stems.
Quantity of bloom: Abundant in greenhouse.
Continuity: Continuous in greenhouse.
Fragrance: Strong; spicy.
Bud:
*Peduncle.*—Long; heavy; erect; medium green; almost smooth; few hairs; yellow.
Before calyx breaks:
*Size.*—Large.
*Form.*—Long pointed; with foliaceous appendages on the surface of the bud extending beyond the tip of the bud equal to one-fourth of its length.
As calyx breaks:
*Color.*—53-A.
As first petal opens:
*Size.*—Large.
*Form.*—Long pointed.
*Color.*—Outside: Fan 1 53-D. Inside: Fan 1 53-B.
Opening: It opens up well.
Bloom:

*Size when fully open.*—Large, 5" to 7".

*Petalage.*—Very double; from 28 to 34 petals; arranged regularly.

*Form.*—Very centered at first becoming high centered; petals at first being tightly rolled inward; becoming later at maturity loosely rolled outward.

Petals: Medium thick; with inside velvety; outside satiny.

*Shape.*—Outer: obvate with flat base. Intermediate: obvate; scalloped with round apex with single tooth. Inner: obvate; scalloped with round apex with single tooth.

*Color.*—Color of newly opened flowers: Outer petal: Outside surface: Fan 2 58-B. Inside surface: Fan 1 46-C. Intermediate petal: Outside surface: Fan 2 58-C. Inside surface: Fan 1 46-D. Inner petal: Outside surface: Fan 2 58-B. Inside surface: Fan 1 45-D. Color of flower three days after opening: Outer petal: Outside surface: Fan 2 57-C. Inside surface: Fan 2 53-D. Inner petal: Outside surface: Fan 2 64-C. Inside surface: Fan 2 53-C.

General Color Effect:

*Newly open flower.*—A vibrant solid reddish-pink color without any variance over the entire flower.

*Flowers three days open.*—Color becomes a little darker in the center with a slight lightening toward the outside of the petals.

Behavior: Petals drop off cleanly.

Flower longevity: Cut flowers grown in greenhouse keep at livingroom temperature 8 days during November.

REPRODUCTIVE ORGANS

Stamens: Many; arranged irregularly about pistils.

*Filaments.*—Many; most with anthers; medium length.

*Color.*—Yellow group 4-C.

*Anthers.*—Open at various times; medium length. Color: yellow group 1-C. Occasionally an anther fused with a petaloid.

*Pollen.*—Moderate; lemon-yellow.

*Pistils.*—Many.

*Styles.*—Uneven; medium length; medium weight; loosely bunched.

*Stigma.*—Yellow.

*Ovaries.*—Some protruding from receptacle.

*Hips.*—Medium length globular pear-shaped; very smooth; walls thick; fleshy; russet.

*Sepals.*—Falling soon; moderately long; spear-shaped, recurved.

*Seeds.*—Medium number; large.

PLANT

Foliage:

*Leaves.*—Compound of three, five or seven leaflets; moderately abundant; large; leathery; average five-leaflet leaf is 7 inches long and 5 to 6 inches wide.

*Leaflets.*—Ovate with acute base obtuse margin simply serratentate.

*Color.*—Mature upper surface: Yellow-green Group 147-A. Mature under surface: Greyed-green group 191-A. Young upper surface: Green Group 137-A. Young under surface: Greyed-green Group 191-A.

*Rachis.*—Medium weight. Upper side: Grooved. Under side: Sparsely thorny.

*Stipules.*—Moderately long; narrow; moderately short points; turning out an angle of less than 90°.

*Disease.*—Resistance comparable to the average variety growing under the same conditions.

Growth:

*Habit.*—Upright.

*Growth.*—Moderately vigorous in the greenhouse; in outdoor culture the bush averages 48 inches in height and 36 inches in width.

*Canes.*—Heavy.

*Main stems.*—Dull. Color: Green Group 137-B. Prickles: Several. Color: Greyed-orange Group 174-A. Hairs: None.

*Branches.*—Bright. Color: Green Group 137-C. Prickles: Several. Color: Greyed-green Group 195-A. Hairs: None.

*New shoots.*—Bright. Color: Green Group 137-D. Prickles: Few. Color: Yellow-green Group 147-C. Hairs: None.

What is claimed is:

1. A new and distinct variety of rose plant of the hydrid tea class found as a sport of a rose plant entitled "Duchess" characterized by its vibrant reddish-pink color which is substantially maintained from flower opening through petal drop, and its ability to yield flowers on a continuous basis when grown in a greenhouse, substantially as shown and described.

* * * * *

UNITED STATES PATENT AND TRADEMARK OFFICE

CERTIFICATE OF CORRECTION

PATENT NO. : PPO,7995

DATED : October 6, 1992

INVENTOR(S) : Glen Strahle

It is certified that error appears in the above-identified patent and that said Letters Patent is hereby corrected as shown below:

On the title page, item (54), delete "plane" and insert --plant--.

Col. 1, Line 27 : delete "establishes" insert -- established --

Signed and Sealed this

Twenty-eighth Day of September, 1993

Bruce Lehman

*Attest:*

BRUCE LEHMAN

*Attesting Officer*

*Commissioner of Patents and Trademarks*